United States Patent [19]

Dulebohn

[11] Patent Number: 5,176,695
[45] Date of Patent: Jan. 5, 1993

[54] SURGICAL CUTTING MEANS

[75] Inventor: David H. Dulebohn, Tonka Bay, Minn.

[73] Assignee: Davinci Medical, Inc., Plymouth, Minn.

[21] Appl. No.: 726,978

[22] Filed: Jul. 8, 1991

[51] Int. Cl.⁵ ............................................. A61B 17/00
[52] U.S. Cl. ..................................... 606/170; 30/134; 30/241
[58] Field of Search ................... 606/83, 79, 110, 167, 606/170, 137, 171, 174; 30/258, 241, 242, 243, 134; 128/750–755, 898

[56] References Cited

U.S. PATENT DOCUMENTS

| 253,359 | 2/1882 | Ewing | 606/174 |
| 719,799 | 2/1903 | Hill | 30/241 |
| 1,324,976 | 12/1919 | Oesterwitz | 606/110 |
| 2,541,063 | 2/1951 | Hubbard | 30/134 |

Primary Examiner—C. Fred Rosenbaum
Assistant Examiner—William W. Lewis
Attorney, Agent, or Firm—Zarley, McKee, Thomte, Voorhees, & Sease

[57] ABSTRACT

A surgical cutter, basically designed for but not limited to laparoscopic surgery, contains a slotted housing and a linearly reciprocating blade which moves parallel to the longitudinal axis of the housing within the slot. The housing also contains a shaped opening near the distal end, the surfaces of this opening being generally perpendicular to the plane of the slot in the housing. Portions of the shaped opening surfaces co-act with the cutting edge of the blade to confine the material to be cut so that it is confined, supported, and cleaved as the blade moves through the plane of the co-acting supporting surface in the opening. The cutting edge of the blade is enveloped by the housing at both ends of the cutting stroke so that the instrument can be safely inserted into and used within the patients body without spurious cutting or damage to the blade.

13 Claims, 2 Drawing Sheets

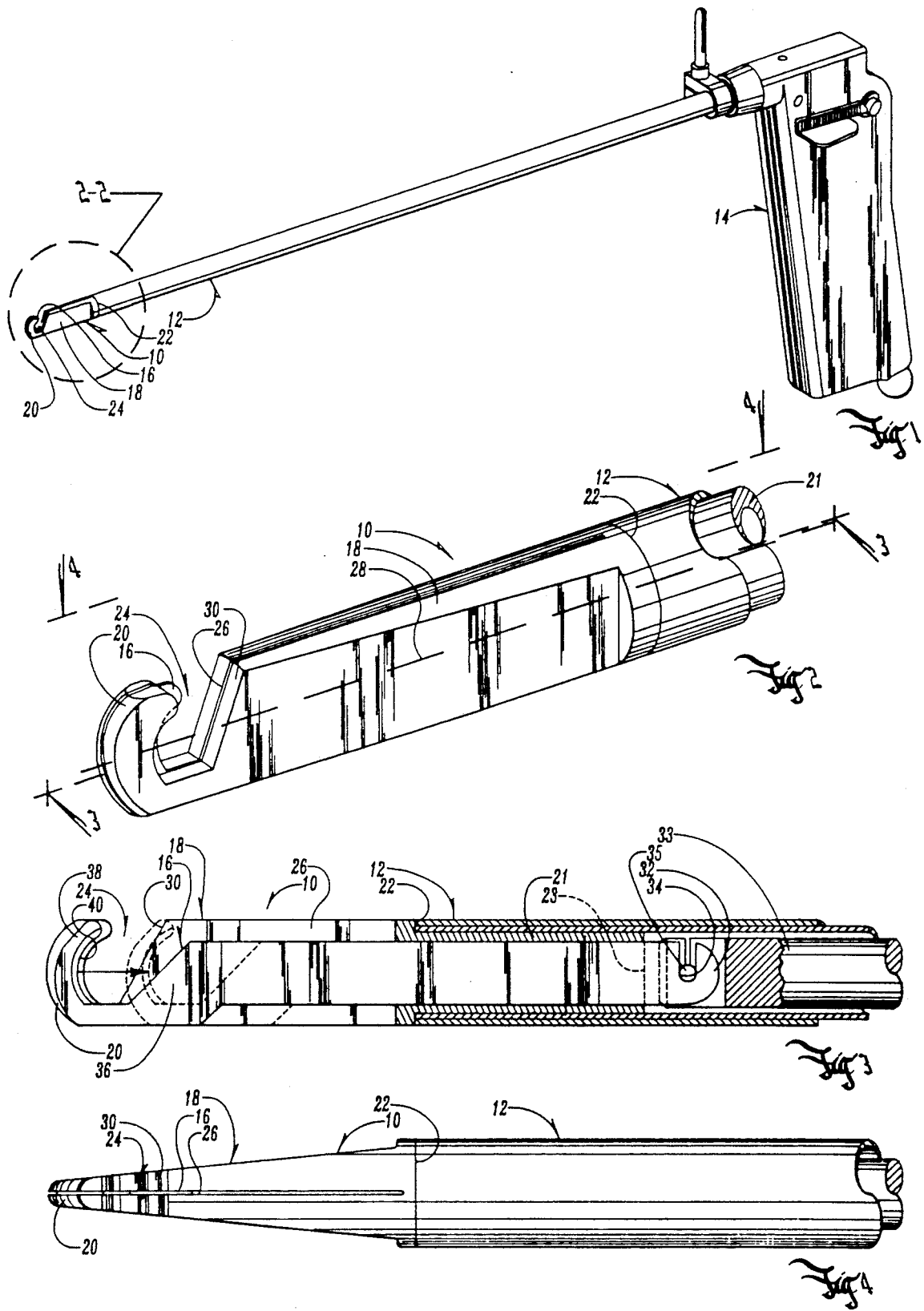

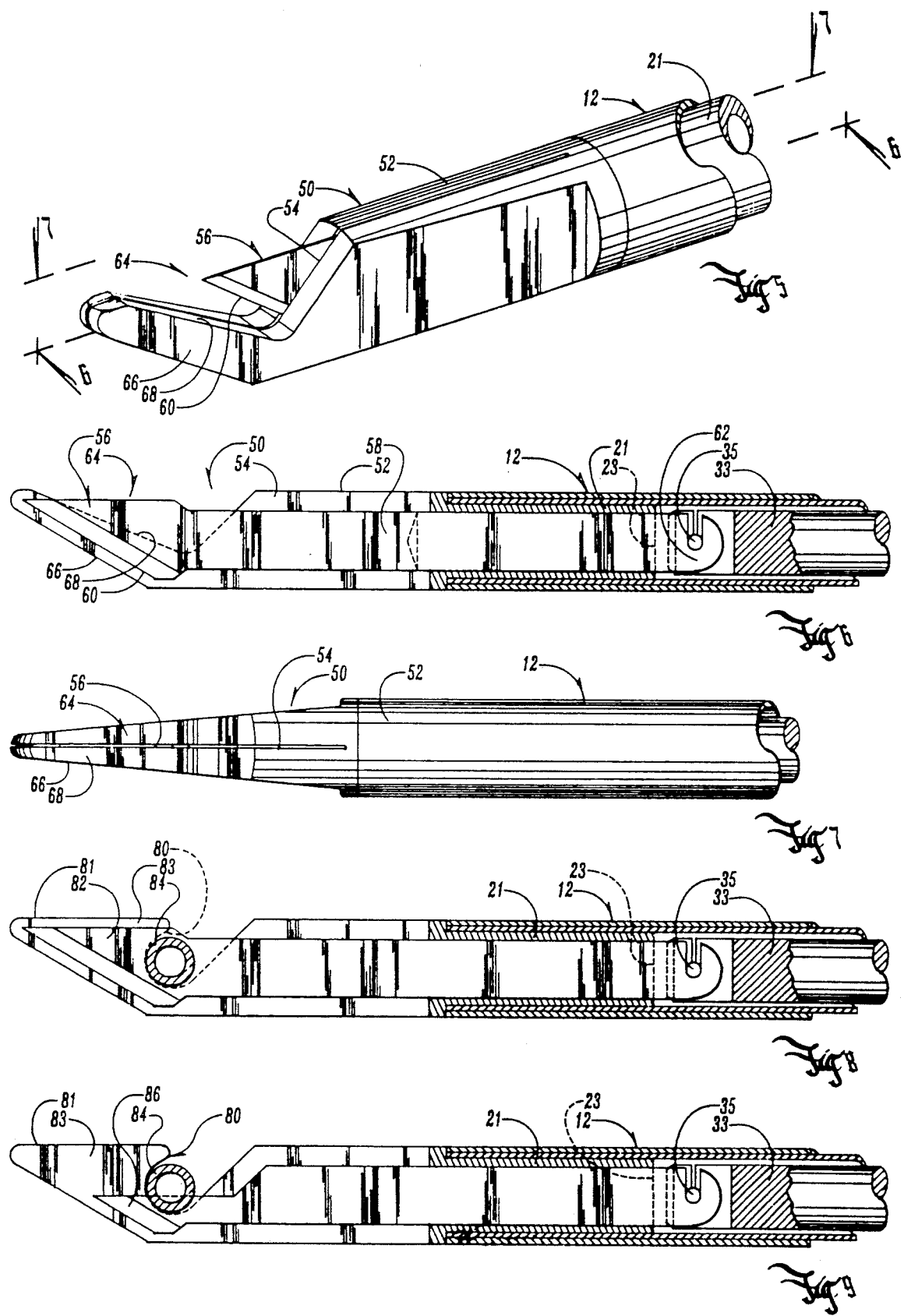

SURGICAL CUTTING MEANS

BACKGROUND OF THE INVENTION

A. Field of Invention

The present invention relates to surgical cutting instruments, and particularly to cutting instruments for laparoscopic surgery, where the instrument is inserted and withdrawn through a very small tube, which is inserted through a very small laparotomy.

B. Problems in the Art

A wide range of cutting needs exist in surgery. Different instruments have been developed to attempt to meet these needs. Examples include scalpels, scissors, wire loop cutters and saws.

These type of cutters have generally satisfied the types of cutting procedures needed in most types of surgery. However, as medical procedures change and become more sophisticated, the types of cutters and methods for using them change.

Recently, a combination of technology and techniques have allowed some surgical procedures to be performed less traumatically and invasively with respect to the patient's body. In other words, instead of requiring a large incision, or combination of incisions to more less open up the patient to gain access to interior organs, vessels, or areas, some procedures can be accomplished through a combination of very small openings. Technology such as fiber optic lighting, laparoscops, and very small cameras are utilized to allow the surgeon to view internal areas of the body through a very small tube either directly or on a television screen. The small tube is usually referred to as a cannula or a trocar. The primary advantage to this type of surgery is a substantial decrease in the amount of time needed for the patient's recovery. Large incisions through substantial parts of the patient's body require weeks and months of recovery time. If the invasion into the body is made through small holes or openings, however, this can be reduced quite significantly.

A very practical problem regarding instrumentation is created, however. The size of the small opening into the patient limits the size of the instrument that can be moved to the location within the patient's body. It also affects the mechanics of how the instrument can be operated.

Still further, such procedures represent a drastic shift in the frame of reference of the surgeon. The surgeon must view a television screen instead of viewing directly the surgical location, the instruments tips and the surgeon's interaction with the instruments. This impacts on what type of instruments are best for these procedures.

Laparoscopic cholecystectomy is an example of this type of surgery. Small incisions of only 5 and 10 MM (millimeters) are made in the patient's abdomen. Gallbladder removal involves cutting the ducts leading to the gallbladder. A laparoscope combined with a small camera is inserted through a 10 MM trocar and the internal area of interest is then televised for the surgeon.

There is risk in cutting requirements, such as the ducts associated with the gallbladder. It is imperative that the surgeon isolates and positively identifies the duct. The duct must be held in the isolated position during cutting, and this is difficult to accomplish with scissors.

Other types of laparoscopic surgery, where instruments are inserted through a small incision, or even simply surgery which requires reliable cutting of small portions, may experience these same problems. Less invasive types of surgery therefore has created the need for a better type of surgical cutting instrument.

It is therefore a principal object of the present invention to provide a surgical cutting means which improves over or solves the deficiencies and problems in the art.

Another object of the present invention is to provide a surgical cutting means which provides a reliable cutting action for specific types of cutting requirements of small items or portions of items.

Another object of the present invention is to provide a surgical cutting means which is easy to operate, and is capable of holding the element to be cut during cutting.

Another object of the present invention is to provide a surgical cutting means which shrouds the sharp cutting blade to prevent damage to the blade during insertion and removal through a small trocar.

Another object of the present invention is to provide a safe means of inserting the instrument into the patient thus preventing spurious cutting.

Another object of the present invention is to provide a shroud after cutting so that the sharp blade will not cut anything beyond the cutting stroke.

A still further object of the present invention is to provide a surgical cutting means which isolates the object to be cut before the cutting stroke is executed.

Another object of the present invention is to provide a surgical cutting means which can be inserted deep into the body cavity, operated, and withdrawn, without damage to the patient.

Still further object of the present invention is to provide a surgical cutting means which is easy to maintain and repair.

Another object of the present invention is to provide a surgical cutting means which is efficient, economical, and durable.

These and other objects features, and advantages of the present invention will become more apparent with reference to the accompanying specification and claims.

SUMMARY OF THE INVENTION

The present invention includes surgical cutting means which is attachable to an actuator means which provides linear reciprocating movement to the blade of the cutting means. A housing or body of small cross sectional diameter and an elongated shape includes guides to retain and control the movement of the blade.

An opening exists along the housing. The cutter is maneuvered so that the material to be cut is at least partially positioned in the opening. The cutting edge of the blade is then passed at least partially through the opening to make the desired cut in the material.

The blade is generally flat and has a cutting edge. The form and location of the cutting edge can vary. For example the cutting edge can either be on the blade's forward outer edge, or the blade can have a hook shaped portion with the cutting edge facing back towards the opposite end of the cutter. Other configurations are possible. Depending on the position of the cutting edge, cutting is accomplished by either passing the cutting edge of the blade from a proximal position to a distal position of the cutter through the opening, or from a distal position to a proximal position through the opening. In either case, the housing and opening serve to retain the material to be cut against the force of the blade to insure a reliable cut.

The surgical cutter of the present invention basically comprises a cleaver blade within a housing assembly. The housing assembly serves to retain the blade, to guide the cleaver blade, to enclose the cutting blade when in extended and retracted positions, and to capture and hold material to be cut. The portions of the housing defining the opening can also serve as a back stop against which the material can be cut. This is a prime advantage over scissors which do not have any sort of capturing, isolating, or back-stop capabilities.

BRIEF DESCRIPTION OF THE DRAWINGS

FIG. 1 is a perspective view of an embodiment of the invention attached to an actuator handle.

FIG. 2 is an enlargement taken along line 2—2 of FIG. 1 isolating the embodiment according to the invention.

FIG. 3 is a cross sectional elevational view taken along line 3—3 of FIG. 2.

FIG. 4 is a top plan view taken along line 4—4 of FIG. 2.

FIG. 5 is an enlarged perspective isolated view of an alternative embodiment according to the invention.

FIG. 6 is a sectional view taken along line 6—6 of FIG. 5.

FIG. 7 is a top plan view taken along line 7—7 of FIG. 5.

FIG. 8 is a side cross sectional elevational view of a still further embodiment of the present invention.

FIG. 9 is a side cross sectional elevational view of another embodiment of the present invention.

DETAILED DESCRIPTION OF THE PREFERRED EMBODIMENT

To assist in a better understanding of the invention, a particular embodiment or embodiments of the invention will now be described. It is to be understood that the invention is not limited to this description, which is only presented for illustrative purposes.

The drawings will be referred to in this description. Specific parts and locations in the drawings will be identified with reference numerals. The same reference numerals will be utilized for the same parts or locations throughout the drawings unless otherwise noted.

FIGS. 1-4 depict one embodiment according to the invention. Cleaver cutter assembly 10 is attached to an extension 12, which in turn is connected to actuator 14. Cutter 10 is connected to extension 12 by means such as are well known in the art. For example, a releasable junction between cutter 10 and extension 12 could be made by using removable pins or keys. Actuator 14 provides linear movement of a rod (see reference number 33 in FIG. 3) within extension 12. This linear movement in turn is utilized by cutter 10 to move blade 16 in a linear fashion along the longitudinal axis of extension 12.

As previously discussed, cutter 10, extension 12, and actuator 14 can be utilized to enter a patient's body cavity by inserting cutter 10 and part of extension 12 through a trocar in the patient's body wall. Actuator 14 then exists outside the patient's body and is manipulated by the surgeon to position cutter 10 and to cause cutting action.

In the embodiment shown in FIG. 1, the diameter of extension 12 and cleaver cutter 10 is approximately one half centimeter.

FIGS. 2 and 3 show that cutter 10 has an elongated housing or body 18 with a distal end 20 and a proximal end that extends past shoulder 22 into 12. An opening 24 exists along housing 18 between end 20 and shoulder 22.

By referring to FIG. 2, an enlarged perspective of cutter 10 is shown. A slot 26 extends along longitudinal axis 28 of cutter 10 basically bisecting a portion of housing 18. Distal end 20 has a C-shape which is curved back towards the remainder of housing 18. Opening 24 is substantial in that it basically exposes a majority of the cross sectional area of housing 18 between portion 30 and distal end 20. The outer side of distal end 20 is rounded to be atraumatic to the patient. Distal end 20 also completely envelopes blade 16 to prevent any damage to the blade or cutting of the patient prior to the surgeon stroking the blade.

FIGS. 3 and 4, illustrate how blade 16 is positioned within housing 18. Slot 26 basically serves as a guide for blade 16. As shown in FIG. 3, proximal end of 32 of blade 16 has an aperture 34 which allows its connection to the drive rod 33 (by pin 35). Aperture 34 allows blade 16 to be connected to the drive rod 33 so that it can be linearly reciprocated along longitudinal axis 28 in housing 18. It is to be understood that slot 26 extends from the very distal end 20 almost entirely to the shoulder 22 of housing 18. The portion 21 of housing 18 between shoulder 22 and proximal end 23 is completely cylindrical and therefore retains blade 16, and assists in causing it to reciprocate parallel to the longitudinal axis of housing 18. The width of slot 26 is slightly larger than the cross sectional width of blade 16.

FIG. 3 shows that blade 16 has a main portion 36 and then a hook shaped portion 38 which is offset from the main extension 36. Cutting edge 40 is on the interior side of hook shaped portion 38.

In the normal position, blade 16 is positioned as shown in solid lines in FIG. 3. The hook shaped portion 38 is housed within distal end 20 so that the cutting edge is not exposed. To provide a cutting stroke, blade 16 is moved proximally with respect to housing 18 to move hook shaped portion 38 through opening 24 to an opposite position also substantially within housing 12 as shown in dashed lines in FIG. 3. The material to be cut must therefore be positioned in opening 24, and cutter 10 must be manipulated so that this relationship occurs. Cutting edge 40 would therefore be pulled through the material to be cut. Hook shaped portion 38 could then be returned to the normal position for another cutting stroke. Portion 30, see FIGS. 2 and 3, serves as a rigid back stop or retaining wall to assist in holding the material to be cut in position. Hook shaped portion 38 of blade 16 also serves to hold the material in place while cutting. This cooperation assures the cutting performance of cutter 10.

Blade 16 therefore basically acts as a clever to cut through tissue, ducts, blood vessels, or other items or materials. The portions of housing 18 surrounding and defining opening 24, act as a type of hook to isolate the object to be cut and as a platform for the cleaver to co-act with. This relationship of components therefore presents an improved way to cut, within the limitations of the very small diameter trocar through which the instrument must be inserted.

Blade 16 can be made of several materials known within the art. One example would be hard stainless steel. Housing 18 can be made of a number of materials known within the art.

Additionally, it can be understood that this type of relationship of components provides for safe operation. In essence, the surgeon only needs to make sure the appropriate tissue or material is placed within opening 24, and then the linear, smooth, highly controllable cutting of the retained material can be easily accomplished, even when viewing the procedure on a video screen, instead of directly. The retention of the materials to be cut within opening 24 also allows cuter 10 to be better equipped to cut tough or sinewy material.

FIGS. 5-7 show an alternative embodiment according to the present invention. It is similar to cleaver cutter 10 in most respects except as described below.

In FIG. 5, cleaver cutter assembly 50 is shown. Housing 52 contains a slot 54 to guide blade 56. A major difference from cutter 10 is that blade 56, as shown in FIG. 6, is basically quadrilateral in nature and has a straight cutting edge 60 at the distal end of blade 56. Additionally, opening 64 is differently configured than opening 24 of cutter 10, as is distal end 66 of housing 52.

As can be seen by referring to FIGS. 5-7, in this instance the material to be cut must again be brought into opening 64. Cutting is accomplished by moving cutting edge 60 of blade 56 from its normal position (retracted proximally into housing 52) across opening 64 through plane 68 of end 66 (to the position shown in FIG. 6). Blade 56 is therefore pushed instead of pulled through the cutting stroke.

Cutters 10 and 50 therefore present different configurations that can be used for different types of cutting as desired by the surgeon. For example, cutter 10 is preferable for cutting ducts or blood vessels because the curved hook shaped end and blade can better isolate and retain a rounded item. Cutter 50 might be better for separating and cutting membranes. For example, a web-like structure is associated with the connection of the gallbladder to the liver and cutter 50 could pry between these organs and sever the connections. Cutter 50 could therefore allow the surgeon to lift and cut portions of this web one at a time as in nibbling, rather than going behind it and hooking it with cutter 10 and pulling on the web. Again, cutter 50 utilizes portions of the housing 52 defining opening 64, and especially plane 68, as a co-acting surface for supporting and holding the membrane as cutting edge 60 passes through plane 68.

It can therefore be seen that the basic invention utilizes an elongated tubular housing. A flat planar blade is positioned within a slot extending along the longitudinal axis of the housing. An opening along the housing near the distal end exposes the blade when the blade is moved toward the distal end. The opening also functions to help retain material to be cut as the blade is pushing against it and cutting through it.

It will therefore be appreciated and understood that the preferred embodiments of the invention do not limit the scope of the invention which is defined solely by the claims which follow. The invention can take on different forms and embodiments while staying within the scope of those claims.

For example, FIGS. 8 and 9 show alterations in the configuration of the cutter according to the invention. In FIG. 8, a different housing shape is utilized. It includes a blunt distal end 81 as well as a shaped portion 80. However, a blade similar to blade 56 in the embodiment of FIGS. 5-7 is utilized. The embodiment of FIG. 8 utilizes the hook shaped portion 80 specifically to hook a duct or blood vessel. Blade 82 is the pushed through duct 84 to cleanly and reliably cut it in two.

FIG. 9 shows essentially the same configuration as FIG. 8, except that the height of blade 86 is much lower than blade 82 in FIG. 8. This allows blade 86 to basically nick or partially cut vessel 84 without severing the entire vessel. This is desirable for various purposes in different surgical procedures.

Additional configurations are possible with regard to the blade and stationary cooperating opening.

What is claimed is:

1. A surgical cutter for insertion and withdrawal through a small opening comprising:

a housing means having a distal end, a proximal end, a side wall, a relatively small cross-sectional diameter, and a longitudinal axis;

an elongated planar blade means having first and second ends which is movable between first and second positions in the housing means;

a confining means associated with the housing means for guiding movement of the blade means generally along the longitudinal axis;

attachment means for connecting the second end of the blade means to a means for moving the blade means;

a cutting edge associated with the first end of the blade means;

an opening along the side wall between the distal and proximal ends of the housing means bounded by front, rear, and opposite intermediate portions in the housing means;

the opening allowing material to be cut to be inserted into the opening when the blade means is in first position, and one of the front or rear portions of the opening serving to provide a back stop for cutting the material when moving the blade means to the second position, the blade means when in the first position is substantially within the housing means out of the opening and towards the proximal end of the housing means, the cutting edge of the blade means when in the second position is substantially in the distal end of the housing means out of the opening.

2. A surgical cutter for insertion and withdrawal through a small opening comprising:

a housing means having a distal end, a proximal end, a side wall, a relatively small cross-sectional diameter, and a longitudinal axis;

an elongated planar blade means having first and second ends which is movable between first and second positions in the housing means;

a confining means associated with the housing means for guiding movement of the blade means generally along the longitudinal axis;

attachment means for connecting the second end of the blade means to a means for moving the blade means;

a cutting edge associated with the first end of the blade means;

an opening along the side wall between the distal and proximal ends of the housing means bounded by front, rear, and opposite intermediate portions in the housing means;

the opening allowing material to be cut to be inserted into the opening when the blade means is in first position, and one of the front or rear portions of the opening serving to provide a back stop for cutting the material when moving the blade means to the second position, the first end of the blade means including a cutting edge oriented towards the proximal end of the housing means.

3. The cutter of claim 2 wherein the first end of the blade means includes a C-shaped portion, the distal side of which is convex, the proximal side of which is concave and contains the cutting edge.

4. The cutter of claim 2 wherein the C-shaped portion and cutting edge of the blade means in the first position is substantially within the distal end of the housing means out of the opening.

5. The cutter of claim 2 wherein the blade means in the second position is substantially in the first end of the housing means out of the opening and towards the proximal end of the housing means.

6. A method of surgically cutting material such as tissue, ducts, blood vessels, or other internal items of the patient comprising:

surgically forming a small aperture into the patient's body cavity;

inserting an elongated housing which carries a planar cutting blade having a cutting edge through the aperture, the housing having an external diameter smaller than the aperture, and having surfaces defining a partially exposed portion along its length;

maneuvering the housing so that the material is located in the partially exposed portion of the housing;

moving the cutting edge of the blade in the housing so that it passes at least partially through the partially exposed portion to at least partially cut any material which is held in position, the cutting edge of the blade pushing the material against a surface of the housing defining the partially exposed portion of the housing while cutting, the surface being generally perpendicular to the plane of the blade.

7. The method of claim 6 wherein the aperture is on the order of 10 millimeters or less in width.

8. The method of claim 6 wherein the housing is elongated and cylindrical.

9. The method of claim 6 wherein the housing has distal and proximal ends.

10. The method of claim 9 wherein the cutting edge of the blade moves from the distal end towards the proximal end of the housing.

11. The method of claim 9 wherein the cutting edge of the blade moves from nearer the proximal end towards the distal end of the housing.

12. The method of claim 6 wherein the cutting edge of the blade is C-shaped.

13. The method of claim 6 wherein the cutting edge of the blade is straight.

* * * * *